(12) United States Patent
Bonger et al.

(10) Patent No.: US 9,115,184 B2
(45) Date of Patent: Aug. 25, 2015

(54) LIGHT-INDUCIBLE SYSTEM FOR REGULATING PROTEIN STABILITY

(71) Applicant: The Board of Trustees Of The Leland Stanford Junior University, Stanford, CA (US)

(72) Inventors: Kimberly M. Bonger, Nijmegen (NL); Rishi Rakhit, Menlo Park, CA (US); Thomas J. Wandless, Menlo Park, CA (US)

(73) Assignee: The Board of Trustees of The Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/194,052

(22) Filed: Feb. 28, 2014

(65) Prior Publication Data

US 2014/0249295 A1    Sep. 4, 2014

Related U.S. Application Data

(60) Provisional application No. 61/771,753, filed on Mar. 1, 2013.

(51) Int. Cl.
| | |
|---|---|
| C07H 21/04 | (2006.01) |
| C12P 21/04 | (2006.01) |
| C12N 5/07 | (2010.01) |
| C12N 5/10 | (2006.01) |
| C07K 1/00 | (2006.01) |
| C07K 14/00 | (2006.01) |
| C07K 17/00 | (2006.01) |
| C07K 7/08 | (2006.01) |
| C07K 14/005 | (2006.01) |

(52) U.S. Cl.
CPC ............ *C07K 14/001* (2013.01); *C07K 7/08* (2013.01); *C07K 14/005* (2013.01)

(58) Field of Classification Search
None
See application file for complete search history.

(56) References Cited

U.S. PATENT DOCUMENTS

| 8,173,792 B2 | 5/2012 | Wandless et al. | |
|---|---|---|---|
| 2010/0034777 A1 | 2/2010 | Wandless et al. | |
| 2012/0178168 A1 | 7/2012 | Wandless et al. | |
| 2013/0116165 A1* | 5/2013 | Schmidt et al. | 514/1.1 |

OTHER PUBLICATIONS

Peter E, et al. Nat. Communications 1:122, Nov. 2010.*
The Stratagene Catalog, p. 39, 1988.*
Wu YI et al. Nature, 461(7260):104-108, Sep. 3, 2009. Available online at—doi:10.1038/nature08241.*
Banaszynski et al., "Conditional control of protein function", Chem. Biol., vol. 13, No. 1, pp. 11-21 (2006).
Bonger et al., "Small-molecule displacement of a cryptic degron causes conditional protein degradation", Nat. Chem. Biol., vol. 7, No. 8, pp. 531-537 (2011).

* cited by examiner

*Primary Examiner* — Robert Landsman
(74) *Attorney, Agent, or Firm* — Judy M. Mohr; McDermott Will & Emery LLP

(57) ABSTRACT

Disclosed herein are a light-inducible system and method for rapidly and reversibly modulating protein stability and function. This system and method employs conditionally stable protein domains that regulate the degradation of a fusion protein depending upon the presence or absence of a particular light source.

17 Claims, 7 Drawing Sheets

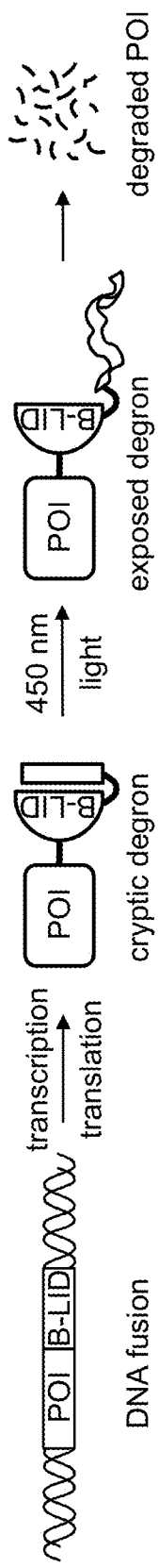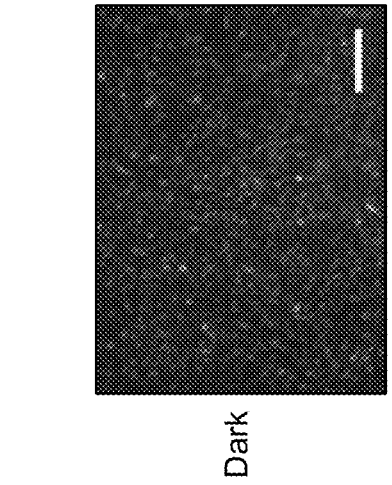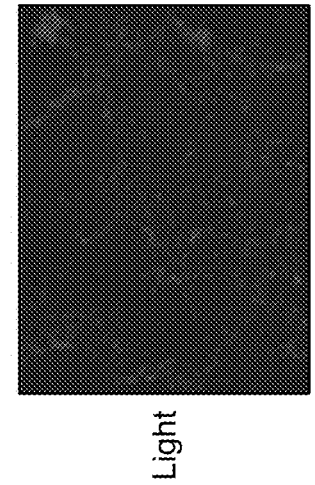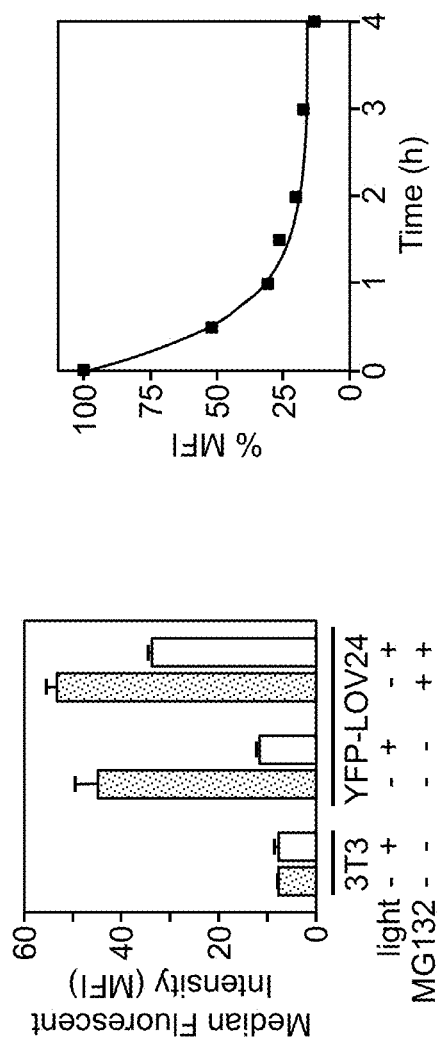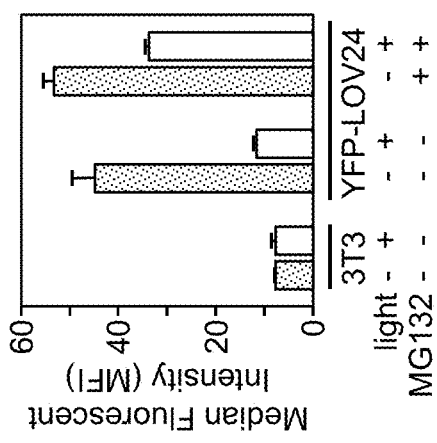
FIG. 1A
FIG. 1B
FIG. 1C
FIG. 1D

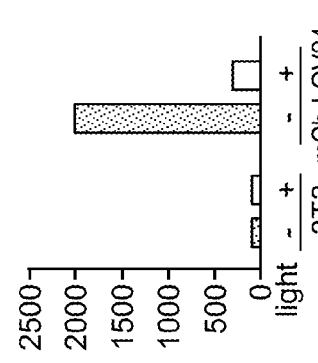
FIG. 2B
FIG. 2C
FIG. 2E
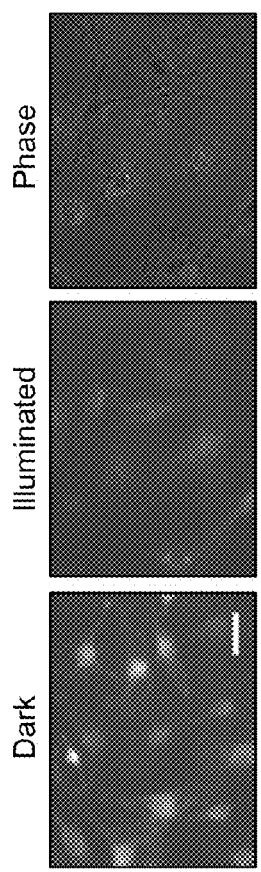
FIG. 2A
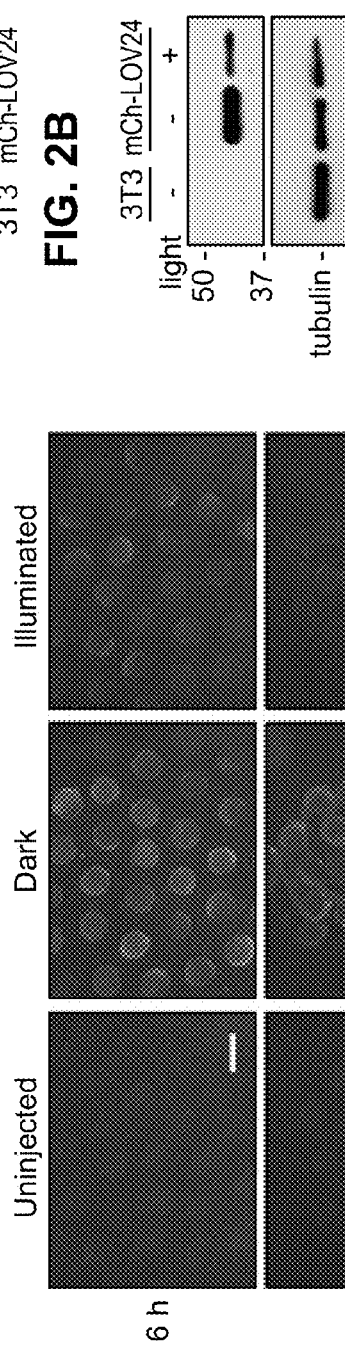
FIG. 2D

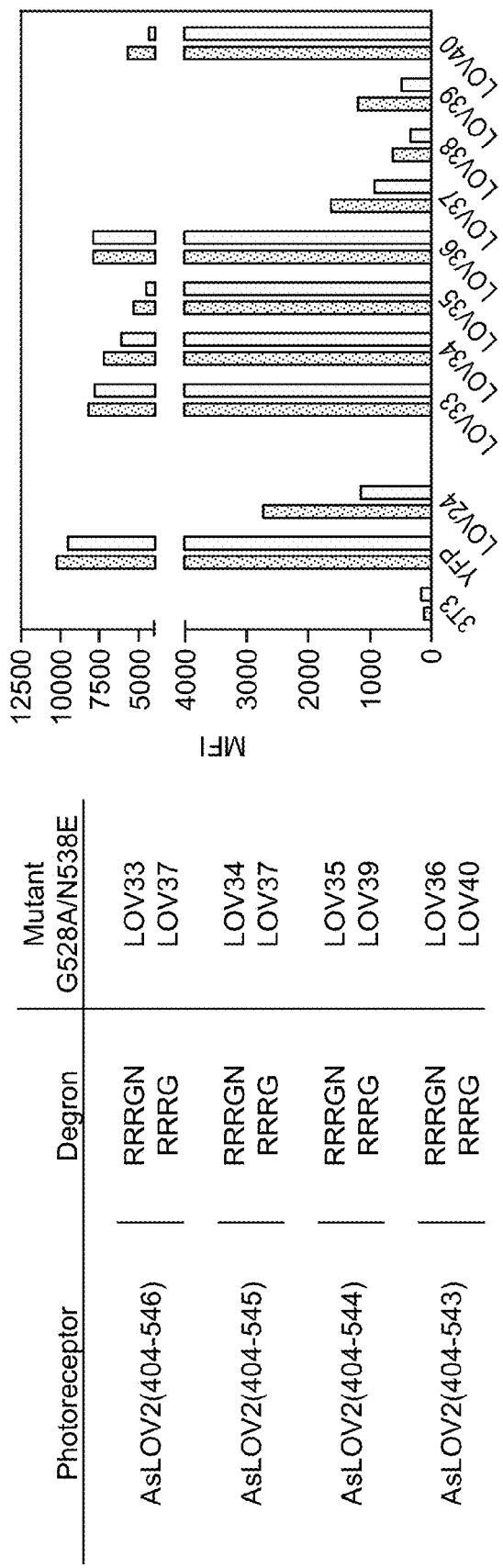

SEQUENCE LISTING

```
<160> NUMBER OF SEQ ID NOS: 11

<210> SEQ ID NO 1
<211> LENGTH: 19
<212> TYPE: PRT
<213> ORGANISM: Artificial
<220> FEATURE:
<223> OTHER INFORMATION: synthesized

<400> SEQUENCE: 1

Thr Arg Gly Val Glu Glu Val Ala Glu Gly Val Val Leu Leu Arg Arg
1               5                   10                  15

Arg Gly Asn

<210> SEQ ID NO 2
<211> LENGTH: 4
<212> TYPE: PRT
<213> ORGANISM: Artificial
<220> FEATURE:
<223> OTHER INFORMATION: synthesized

<400> SEQUENCE: 2

Arg Arg Arg Gly
1

<210> SEQ ID NO 3
<211> LENGTH: 145
<212> TYPE: PRT
<213> ORGANISM: Artificial
<220> FEATURE:
<223> OTHER INFORMATION: synthesized

<400> SEQUENCE: 3

Phe Leu Ala Thr Thr Leu Glu Arg Ile Glu Lys Asn Phe Val Ile Thr
1               5                   10                  15

Asp Pro Arg Leu Pro Asp Asn Pro Ile Ile Phe Ala Ser Asp Ser Phe
                20                  25                  30

Leu Gln Leu Thr Glu Tyr Ser Arg Glu Glu Ile Leu Gly Arg Asn Cys
            35                  40                  45

Arg Phe Leu Gln Gly Pro Glu Thr Asp Arg Ala Thr Val Arg Lys Ile
        50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95
```

Met Arg Asp Gln Lys Gly Asp Val Gln Tyr Phe Ile Gly Val Gln Leu
            100                 105                 110

Asp Gly Thr Glu His Val Arg Asp Ala Ala Glu Arg Glu Gly Val Met
            115                 120                 125

Leu Ala Lys Lys Thr Ala Glu Asn Ile Asp Glu Ala Ala Arg Arg Arg
130                 135                 140

Gly
145

<210> SEQ ID NO 4
<211> LENGTH: 144
<212> TYPE: PRT
<213> ORGANISM: Avena sativa

<400> SEQUENCE: 4

Phe Leu Ala Thr Thr Leu Glu Arg Ile Glu Lys Asn Phe Val Ile Thr
1               5                   10                  15

Asp Pro Arg Leu Pro Asp Asn Pro Ile Ile Phe Ala Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu His Val Arg Asp Ala Ala Glu Arg Glu Gly Val Met
            115                 120                 125

Leu Ile Lys Lys Thr Ala Glu Asn Ile Asp Glu Ala Ala Lys Glu Leu
        130                 135                 140

<210> SEQ ID NO 5
<211> LENGTH: 144
<212> TYPE: PRT
<213> ORGANISM: Artificial
<220> FEATURE:
<223> OTHER INFORMATION: synthesized

<400> SEQUENCE: 5

Phe Leu Ala Thr Thr Leu Glu Arg Ile Glu Lys Asn Phe Ile Ile Thr
1               5                   10                  15

Asp Pro Arg Leu Pro Asp Asn Pro Ile Ile Phe Ala Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

```
Asp Gly Thr Glu His Val Arg Asp Ala Ala Glu Arg Glu Gly Val Met
        115                 120                 125

Leu Ile Lys Lys Thr Ala Glu Asn Ile Asp Glu Ala Ala Lys Glu Leu
    130                 135                 140
```

<210> SEQ ID NO 6
<211> LENGTH: 144
<212> TYPE: PRT
<213> ORGANISM: Artificial
<220> FEATURE:
<223> OTHER INFORMATION: synthesized

<400> SEQUENCE: 6

```
Phe Leu Ala Thr Thr Leu Glu Arg Ile Glu Lys Asn Phe Val Ile Thr
1               5                   10                  15

Asp Pro Arg Leu Pro Asp Asn Pro Ile Ile Phe Ala Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu His Val Arg Asp Ala Ala Glu Arg Glu Gly Val Met
        115                 120                 125

Leu Ala Lys Lys Thr Ala Glu Asn Ile Asp Glu Ala Ala Lys Glu Leu
    130                 135                 140
```

<210> SEQ ID NO 7
<211> LENGTH: 144
<212> TYPE: PRT
<213> ORGANISM: Artificial
<220> FEATURE:
<223> OTHER INFORMATION: synthesized

<400> SEQUENCE: 7

```
Phe Leu Ala Thr Thr Leu Glu Arg Ile Glu Lys Asn Phe Ile Ile Thr
1               5                   10                  15

Asp Pro Arg Leu Pro Asp Asn Pro Ile Ile Phe Ala Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu His Val Arg Asp Ala Ala Glu Arg Glu Gly Val Met
        115                 120                 125

Leu Ala Lys Lys Thr Ala Glu Asn Ile Asp Glu Ala Ala Lys Glu Leu
    130                 135                 140
```

<210> SEQ ID NO 8
<211> LENGTH: 144
<212> TYPE: PRT
<213> ORGANISM: Artificial
<220> FEATURE:
<223> OTHER INFORMATION: synthesized

<400> SEQUENCE: 8

Phe Leu Ala Thr Thr Leu Glu Arg Ile Glu Lys Asn Phe Val Ile Thr
1               5                   10                  15

Asp Pro Arg Leu Pro Asp Asn Pro Ile Ile Phe Ala Ser Asp Ser Phe
            20                  25                  30

Leu Gln Leu Thr Glu Tyr Ser Arg Glu Glu Ile Leu Gly Arg Asn Cys
        35                  40                  45

Arg Phe Leu Gln Gly Pro Glu Thr Asp Arg Ala Thr Val Arg Lys Ile
    50                  55                  60

Arg Asp Ala Ile Asp Asn Gln Thr Glu Val Thr Val Gln Leu Ile Asn
65                  70                  75                  80

Tyr Thr Lys Ser Gly Lys Lys Phe Trp Asn Leu Phe His Leu Gln Pro
                85                  90                  95

Met Arg Asp Gln Lys Gly Asp Val Gln Tyr Phe Ile Gly Val Gln Leu
            100                 105                 110

Asp Gly Thr Glu His Val Arg Asp Ala Ala Glu Arg Glu Ala Val Met
        115                 120                 125

Leu Ile Lys Lys Thr Ala Glu Glu Ile Asp Glu Ala Ala Lys Glu Leu
    130                 135                 140

<210> SEQ ID NO 9
<211> LENGTH: 5
<212> TYPE: PRT
<213> ORGANISM: Artificial
<220> FEATURE:
<223> OTHER INFORMATION: synthesized

<400> SEQUENCE: 9

Arg Arg Arg Gly Asn
1               5

<210> SEQ ID NO 10
<211> LENGTH: 5
<212> TYPE: PRT
<213> ORGANISM: Artificial
<220> FEATURE:
<223> OTHER INFORMATION: synthesized

<400> SEQUENCE: 10

Tyr Ala Leu Ala Ala
1               5

<210> SEQ ID NO 11
<211> LENGTH: 6
<212> TYPE: PRT
<213> ORGANISM: Artificial
<220> FEATURE:
<223> OTHER INFORMATION: synthesized

<400> SEQUENCE: 11

Gly Gly Ser Gly Gly Ser
1               5

LIGHT-INDUCIBLE SYSTEM FOR REGULATING PROTEIN STABILITY

CROSS-REFERENCE TO RELATED APPLICATIONS

This application claims the benefit of U.S. Provisional Application No. 61/771,753, filed Mar. 1, 2013, incorporated herein by reference in its entirety.

STATEMENT REGARDING GOVERNMENT INTEREST

This invention made with Government support under contract GM073046 awarded by the National Institutes of Health. The Government has certain rights in this invention.

REFERENCE TO SEQUENCE LISTING, TABLE OR COMPUTER PROGRAM

A Sequence Listing is being submitted electronically via EFS in the form of a text file, created Feb. 28, 2014, and named "091511-0581_ST25.txt" (8,938 bytes), the contents of which are incorporated herein by reference in their entirety.

TECHNICAL FIELD

Compositions, systems and methods for rapidly and reversibly modulating the stability of proteins are described. The coding sequence for a protein of interest is genetically fused to a sequence encoding a stability-affecting single protein domain and the fusion protein thereby encoded is degraded upon exposure to non-toxic light.

BACKGROUND

Techniques for modulating transcription of DNA and RNA expression provide powerful tools for studying specific genes and their biological function. For example, the tet/dox and Cre/lox systems have been widely used to target gene expression at the transcriptional level (Ryding, A. D. S. et al. (2001) *J. Endocrinol.* 171:1-14), and RNA interference provides a method to achieve post-transcriptional gene silencing (Fire. A. et al. (1998) *Nature* 391:806-811; Medema, R. H. (2004) *Biochem. J.* 380:593-603; Raab, R. M. and Stephanopoulos, G. (2004) *Biotechnology & Bioengineering* 88:121-132). Biological studies of mammalian development and physiology have also been greatly aided by techniques allowing the disruption of specific genes using homologous recombination and generation of transgenic mice. However, interpretation of the phenotypes of transgenic or knock-out mice possessing null mutations can be hampered by early embryonic lethality or compensation for the absence of a gene during development. Toward a solution for such problems, methods for conditional gene inactivation have been developed, but often these methods are slow and irreversible. There remains a widespread need for a facile method to reversibly inactivate the protein product of a specific gene rather than permanently knocking-out the gene encoding the protein.

Techniques have also been developed to regulate proteins on a post-translational level. Experimental methods have been developed to regulate protein stability and function rapidly and reversibly using protein domains that are conditionally stable in cultured cells or living animals. Such methods are often controlled by the binding of a small molecule ligand. (Baker, M. *Nat. Methods* 9, 443-447 (2012)). Methods to conditionally regulate protein abundance in cells are useful for biologists to study a protein's function(s) in complex biological systems. However, methods for regulating protein function directly are limited, especially in mammalian cells. Inhibitors or activators of particular proteins have been identified, and often take the form of cell-permeable small molecules. Many of these molecules have found widespread use as biological probes, often because the speed, dosage-dependence, and reversibility of their activities, which complement methods for genetically modulating gene expression (Schreiber, S. L. (2003) *Chem. & Eng. News* 81:51-61). However these inhibitors or activators are often promiscuous, affecting several proteins rather than a specific protein (Davies, S. P. et al. (2000) *Biochem. J.* 351:95-105; Bain, J. et al. (2003) *Biochem. J.* 371:199-204; Godl, K. et al. (2003) *Proc. Natl. Acad. Sci. U.S.A.* 100:15434-15439; Tan, D. S. (2005) *Nat. Chem. Biol.* 1:74-84; Mayer, T. U. et al. (1999) *Science*, 286:971-974).

A method by which specific kinases can be inhibited using a small-molecule modulator has also been developed (Shah et al., 1997; Bishop, A. C. et al. (1998) *Current Biology* 8:257-266). This method involves mutating the protein of interest, typically replacing a large conserved residue in the active site with a smaller residue, such as glycine or alanine. Specificity is achieved by chemically modifying a promiscuous inhibitor to include a bulky side-chain substituent (e.g., R-group), which fills the corresponding cavity in the binding site of the modified protein of interest, while preventing productive interactions with other kinases. While this so-called "bump-hole" approach has been successful both in cultured cells and in mice (Bishop, A. C. et al. (2000) *Nature* 407:395-401; Wang, H. et al. (2003) *Proc. Natl. Acad. Sci. U.S.A.* 100:4287-4292, Chen, X. et al. (2005) *Neuron* 46:13-21), it appears to be limited to ATPases and GTPases. Additional methods are required to probe the function of a wider variety of proteins.

Alternative strategies to perturb protein function by exploiting existing cellular processes have also been devised (Banaszynski, L. A. et al. (2006) *Chem. Biol.* 13:11-21). For example, a method has been developed for controlling protein function based on the importance of certain N-terminal residues for protein stability (Bachmair, A. et al. (1986). *Science* 234:179-186). Szostak and coworkers showed that a small peptide sequence could be fused to the N-terminus of a protein of interest to modulate protein stability (Park, E-C. et al. (1992) *Proc. Natl. Acad. Sci. U.S.A.* 89:1249-1252). Furthermore, dimeric small molecules have been engineered to conditionally target fusion proteins for degradation via E3 ligase or the proteasome, itself (Schneekloth et al., 2004; Janse, D. M. et al. (2004) *J. Biol. Chem.* 279:21415-21420). However, these systems require either a prior knowledge of the high-affinity ligands that modulate the activity of a protein of interest or they are restricted to genetically engineered yeast strains.

An alternative approach for controlling protein function directly is to interfere with subcellular localization. For example, several methods have been developed to regulate protein localization using a small-molecule by taking advantage of the FKBP-rapamycin-FRB ternary complex (Kohler, J. J. and Bertozzi, C. R. (2003) *Chem. Biol.* 10:1303-1331 and Inoue, T. et al. (2005) *Nature Methods* 2:415-418). Rapamycin and FK506 are potent, commercially available immunosuppressive agents, which are ligands of the FK506-binding protein (FKBP12, FKBP). Rapamycin also binds to FKBP-rapamycin-associated protein (FRAP). FRAP is also called the mammalian target of rapamycin (mTOR), rapamycin and FKBP target 1 (RAFT1), and FRB. Rapamycin binds to and inhibits mTOR by interacting with its FKBP-rapamycin-binding (FRB) domain to inhibit/delay G1 cell cycle progression in mammalian cells (see, e.g., Choi, J. et al. (1996) Science 273:239-42 and Vilella-Bach, M. et al. (1999) J. Biol. Chem. 274:4266-72. The FKBP-rapamycin-binding domain is required for FKBP-rapamycin-associated protein kinase activity and GI progression. Fusions of proteins of interest can be made to either FKBP or to the FRP domain of FRAP/mTOR. Colocalization of the protein of interest is induced upon addition of rapamycin. Because rapamycin has inherent biological activity, researchers have developed a "bump-hole" strategy (similar to that employed by Shokat and coworkers), wherein rapamycin derivatives possessing large substituents at the FRB binding interface bind poorly to wild-type FRB and in turn the biologically relevant target FRAP/mTOR, with binding restored upon introduction of compensatory cavity-forming mutations in FRB. Specifically, a C20-methallyl-rapamycin derivative (MaRap) binds to a triple-mutated variant of FRB called FRB* (Liberles, S. D. et al. (1997) Proc. Natl. Acad. Sci. U.S.A. 94:7825-7830).

Recently, methods have been described employing light responsive protein domains. The LOV (Light-Oxygen-Voltage) domains are found in plant photoreceptor proteins and detect blue light via a flavin cofactor. (Herrou, J. & Crosson, S. Nat. Rev. Microbiol. 9, 713-723 (2011)). The LOV2 domain of phototropin 1 from Avena saliva (AsLOV2) possesses a C-terminal alpha helix that is tightly bound to the LOV core domain in the absence of light. Exposure to blue light causes a conformational change of the bound flavin cofactor resulting in unfolding of the helix. The AsLOV2 domain has been used to regulate the activities of certain protein by sterically inhibiting interactions with an effector protein or by conformationally restricting a specific protein conformation. (Wu, Y. I. et al. Nature 461, 104-108 (2009); Lee, J. et al. Science 322, 438-442 (2008); Strickland, D., Moffat, K. & Sosnick, T. R. Proc. Natl. Acad. Sci. USA 105, 10709-10714 (2008)). These methods are suitable for the reported engineered proteins but typically are not generally applicable to any protein-of-interest.

Alternatively, engineered photosensory domains have been used to establish light mediated protein-protein interactions. (Shimizu-Sato, S. et al., Nat. Biotechnol. 20, 1041-1044 (2002); Levskaya, A., et al, Nature 461, 997-1001 (2009); Yazawa, M. et al., Nat. Biotechnol. 27, 941-945 (2009); Kennedy, M. J. et al. Nat. Methods 7, 973-975 (2010); Strickland, D. et al. Nat. Methods 9, 379-384 (2012); Wang, X. et al., Nat. Methods 9, 266-269 (2012); Polstein, L. R. et al., J. Am. Chem. Soc. 134, 16480-16483 (2012); Lungu, O. I., et al. Chem. Biol. 19, 507-517 (2012); Zhou, X. X. et al., Science 338, 810-814 (2012)). Among these, light-induced translocation to the cell or nuclear membrane has been reported to regulate location-specific protein activity and light-induced gene expression, respectively. Light induced protein translocation technologies have been developed based on the interaction of proteins in an activated, lit state (Lungu, et al., Chem. Biol., 19(4):507 (2012)). In addition, technologies for light induced transcriptional activation of a gene of interest has been developed (Wang, X., Nat. Methods 9, 266-269 (2012)). Translocation strategies are, however, limited by the lack of control over protein function once triggered, and they can require two or more genetic manipulations, and existing methods are not suitable for fast and reversible regulation of protein levels in cells, especially using the addition of light. Thus, while the aforementioned methods for regulating protein function directly are noteworthy, a need remains for a convenient, generally useful method (1) for regulating any protein; (2) making use of a single regulatory domain, and that does not require the interaction of multiple proteins; and (3) that is regulated by non-toxic light, such as blue light, so that this technique does not require a small molecule ligand that may have unintended effects. Furthermore, regulation of protein stability in cells in a more spacial or temporal manner may be desirable. A long-felt need remains for improved and novel systems and methods to regulate protein levels and functions directly, rapidly and reversibly using protein domains that are conditionally stable in cultured cells or living animals, particularly in mammalian cells and mammalian organisms.

For tight spatial or temporal control of protein levels, the use of ligands may be undesirable, as the ligands may diffuse freely in cells or organisms and can be hard to remove. The use of light solves such problems and has several advantages over the use of ligands, as it can be delivered nearly instantly and can be applied in a spatially restricted manner to cells or organisms. Light is very suitable as it can be used on specific parts of a cell/mammal and on variable moments as switching to the on and off state is fast. The present disclosure provides a novel single protein regulatory domain that is degraded upon exposure to non-toxic light. The domain is genetically fused to a coding sequence encoding a protein of interest to allow the rapid, light-induced depletion of the fusion product in cells as well as in higher organisms. This technology provides the biological community with tools to directly interrogate protein function in living cells and animals with unprecedented control. This light-inducible technology would facilitate fundamental biological studies as well as more applied advances such as the creation of new and useful animal models of human diseases. With broad applicability, this technology is also useful in the pharmaceutical and biotech industries for validation of potential therapeutic targets.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

Compositions, systems, and methods for modulating the stability of proteins are described. The coding sequence for a protein of interest is genetically fused to a sequence encoding a stability-affecting single protein domain which is degraded upon exposure to non-toxic light.

In one aspect, a light-regulated conditional protein stability system is provided, comprising a nucleic acid sequence encoding a fusion protein that comprises a protein of interest fused in-frame to a sequence encoding a light-responsive, stability-affecting polypeptide domain, and a non-toxic light source, wherein, upon introduction of the nucleic acid sequence to a cell, the fusion protein is expressed, and the stability and levels of the fusion protein can be modulated by exposure of the cells, tissue or organism to a non-toxic light source.

In some embodiments, cells are transformed with the nucleic acid. In some embodiments, eukaryotic cells are transformed with the nucleic acid to produce a stably transformed eukaryotic cell. In some embodiments, the transformed cells are implanted into a living animal. In some embodiments, the transformed cells are implanted into immunodeficient mice as xenografts.

In some embodiments, the nucleic acid sequence is in a viral vector. In some embodiments, the viral vector is a pox virus. In some embodiments, the viral vector is a vaccinia virus.

In some embodiments, the protein of interest is a reporter protein. In some embodiments, the protein of interest is a therapeutic protein.

In some embodiments, the light-regulated, stability-affecting polypeptide comprises an amino acid sequence selected from the group of sequences identified by SEQ ID NOs: 3-8.

In some embodiments, the light-responsive, stability-affecting polypeptide domain destabilizes the protein of interest or fusion protein in the presence of non-toxic light of a particular wavelength. In some embodiments, the non-toxic light has a wavelength of approximately 450-470 nm. In some embodiments, the light-responsive, stability-affecting polypeptide domain does not destabilize the protein of interest in the absence of non-toxic light of a particular wavelength. In some embodiments, the light-responsive, stability-affecting polypeptide domain destabilizes the protein of interest or fusion protein in the presence of non-toxic light of a particular wavelength to a greater degree or extent than it destabilizes the protein of interest or fusion protein in the absence of the non-toxic light.

In some embodiments, the light-responsive, stability-affecting polypeptide destabilizes the protein of interest or fusion protein by causing an increase in the degradation or destruction of the protein of interest or fusion protein when exposed to non-toxic light of a particular wavelength as compared to the level of degradation of the protein of interest or fusion protein when not exposed to the non-toxic light.

In some embodiments, the light-responsive, stability-affecting polypeptide changes the conformation of the fusion protein upon exposure to non-toxic light of a particular wavelength.

In some aspects, a light sensitive degradation domain (DD) is provided, comprising an amino acid sequence selected from the group of sequences identified by SEQ ID NOs: 3-8. In some embodiments, the light sensitive DD comprises SEQ ID NO: 3. In some embodiments, a fusion protein is provided, wherein the fusion protein comprises a light sensitive DD having SEQ ID NO: 3.

In some aspects, a method is provided for conditionally stabilizing a protein of interest, comprising fusing (or providing) a nucleic acid encoding a protein of interest in-frame to a nucleic acid encoding a light-regulated, stability-affecting polypeptide to produce a nucleic acid encoding a fusion protein; introducing the nucleic acid encoding the fusion protein into a cell; expressing the fusion protein in the cell; and exposing the cell to a non-toxic light to destabilize the fusion protein.

In some embodiments of the method, the light-regulated, stability-affecting polypeptide comprises an amino acid sequence selected from the group of sequences identified by SEQ ID NOs: 3-8. In some embodiments of the method, the light-regulated, stability-affecting polypeptide comprises SEQ ID NO: 3.

In some embodiments of the method, the cell is stably transformed with the nucleic acid. In some embodiments of the method, the stably transformed cell is implanted in a living animal. In some embodiments of the method, the nucleic acid sequence is in a viral vector. In some embodiments of the method, the viral vector is a *vaccinia* virus.

In some embodiments of the method, the non-toxic light has a wavelength of approximately 450-470 nm.

In some embodiments of the method, the step of introducing the nucleic acid into a cell comprises infecting the cell with a viral vector comprising the nucleic acid, and implanting the cell into an animal. In some embodiments, the step of introducing the nucleic acid into a cell comprises transfecting a cell of a living animal, in which the cell resides.

In some aspects, provided is a cell comprising a nucleic acid encoding a fusion protein, wherein the fusion protein comprises a protein of interest fused in frame to a light-regulated, stability-affecting polypeptide.

In another aspect, provided is a kit of parts comprising a light-regulated conditional protein stability system, along with instructions for use.

Additional embodiments of the present methods and compositions and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE DRAWINGS

FIGS. 1A-1D show a system for light-induced degradation of proteins.

FIGS. 2A-2C show cells stably transduced with HA-mCherry-LOV24.

FIGS. 2D-2E show zebrafish embryos microinjected with mRNA encoding HA-mCherry-LOV24 demonstrating the usefulness of the B-LID domain for reversible regulation of a protein of interest using non-toxic light.

FIG. 3A shows the various mutant constructs. FIG. 3B compares the Median Fluorescence Intensity (MFI) as measured by analytical flow cytometry of the mutated LOV2 domain constructs.

FIGS. 5A-5B show mutations designed to modulate the interaction between the LOV2 core domain and the degron-containing helix were tested. FIG. 5A shows the nomenclature for the eight mutants tested. FIG. 5B presents the flow cytometric analysis of various domains fused to the C-terminus of eYFP.

BRIEF DESCRIPTION OF THE SEQUENCES

Figures 3A, 3B:
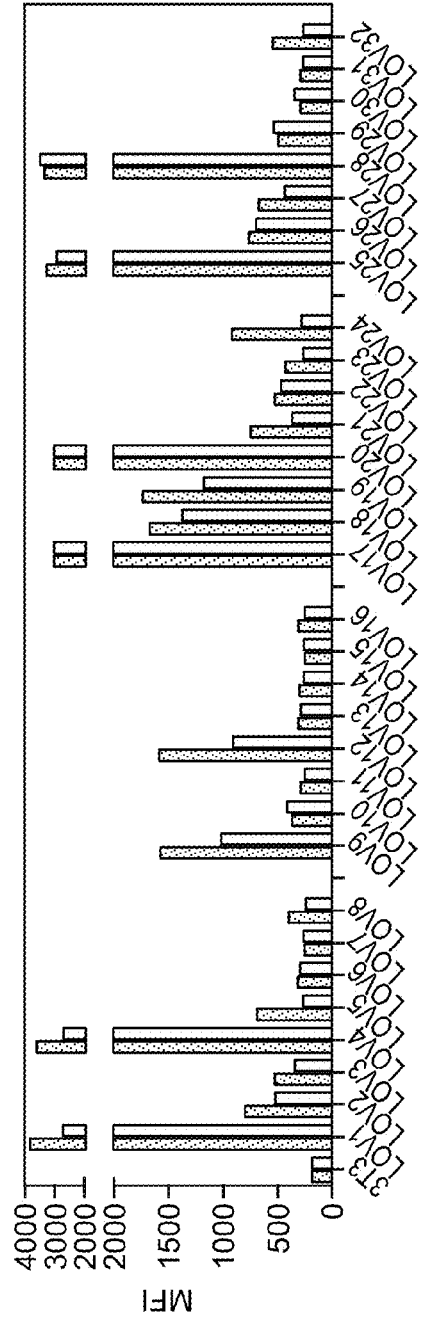
FIG. 3A-3B compare the light-dependent stability of various mutated LOV2 domain proteins possessing a C-terminal degradation domain ("DD," a.k.a. "degron").

SEQ ID NO: 1 presents an exemplary 19-amino acid degron-containing peptide, TRGVEEVAEGVVLLRRRGN (SEQ ID NO: 1).

SEQ ID NO: 2 is an exemplary degron tetrapeptide, RRRG (SEQ ID NO: 2).

SEQ ID NO: 3 is an exemplary light sensitive degradation domain (DD) known as LOV24, having the amino acid sequence:

(SEQ ID NO: 3)
FLATTLERIEKNFVITDPRLPDNPIIFASDSFLQLTEYSREEILGRNCRFL

QGPETDRATVRKIRDAIDNQTEVTVQLINYTKSGKKFWNLFHLQPMRDQKG

DVQYFIGVQLDGTEHVRDAAEREGVMLAKKTAENIDEAARRRG.

SEQ ID NO: 4 shows amino acid residues 404-546 of an AsLOV2 light induced degradation domain of phototropin 1, having the sequence:

(SEQ ID NO: 4)
FLATTLERIEKNFVITDPRLPDNPIIFASDSFLQLTEYSREEILGRNCRFL

QGPETDRATVRKIRDAIDNQTEVTVQLINYTKSGKKFWNLFHLQPMRDQKG

DVQYFIGVQLDGTEHVRDAAEREGVMLIKKTAENIDEAAKEL.

SEQ ID NO: 5 shows the V416I mutation of AsLOV2, wherein the point mutation is underscored and in bold type, having the sequence:

(SEQ ID NO: 5)
FLATTLERIEKNFIITDPRLPDNPIIFASDSFLQLTEYSREEILGRNCRFL

QGPETDRATVRKIRDAIDNQTEVTVQLINYTKSGKKFWNLFHLQPMRDQKG

DVQYFIGVQLDGTEHVRDAAEREGVMLIKKTAENIDEAAKEL.

SEQ ID NO: 6 shows the I532A mutation of AsLOV2, having the sequence:

(SEQ ID NO: 6)
FLATTLERIEKNFVITDPRLPDNPIIFASDSFLQLTEYSREEILGRNCRFL

QGPETDRATVRKIRDAIDNQTEVTVQLINYTKSGKKFWNLFHLQPMRDQKG

DVQYFIGVQLDGTEHVRDAAEREGVMLAKKTAENIDEAAKEL.

SEQ ID NO: 7 shows the V416I/I532A double point mutation of AsLOV2, wherein the point mutations are underscored and in bold type, having the sequence:

(SEQ ID NO: 7)
FLATTLERIEKNFIITDPRLPDNPIIFASDSFLQLTEYSREEILGRNCRFL

QGPETDRATVRKIRDAIDNQTEVTVQLINYTKSGKKFWNLFHLQPMRDQKG

DVQYFIGVQLDGTEHVRDAAEREGVMLAKKTAENIDEAAKEL.

SEQ ID NO: 8 shows the G528A/N538E double point mutation of AsLOV2, having the sequence:

(SEQ ID NO: 8)
FLATTLERIEKNFVITDPRLPDNPIIFASDSFLQLTEYSREEILGRNCRFL

QGPETDRATVRKIRDAIDNQTEVTVQLINYTKSGKKFWNLFHLQPMRDQKG

DVQYFIGVQLDGTEHVRDAAEREAVMLIKKTAEEIDEAAKEL.

SEQ ID NO: 9 is an exemplary degron, RRRGN (SEQ ID NO: 9).

SEQ ID NO: 10 is an exemplary degron, YALAA (SE) ID NO: 10).

SEQ ID NO: 11 is a 6-amino acid linker, GGSGGS, (SEQ ID NO: 11).

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

I. DEFINITIONS

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

When a range of values is provided, it is understood that each intervening value, to the tenth of the unit of the lower limit unless the context clearly dictates otherwise, between the upper and lower limits of that range is also specifically disclosed. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm. Each smaller range between any stated or intervening value in a stated range and any other stated or intervening value in that stated range is encompassed by the disclosure. The upper and lower limits of the smaller ranges may be independently included or excluded in the range, and each range where either, neither or both limits are included in the smaller ranges is also encompassed by the disclosure, subject to any specifically excluded limit in the stated range. Where the stated range includes one or both of the limits, ranges excluding either or both of those included limits are also included.

Examples of other compositions, systems and methods for conditional regulation of protein levels and function are described in U.S. Pat. No. 8,173,792 and U.S. Patent Pre-Grant Publications 2010/0034777 and 2012/0178168, each of which is herein incorporated by reference in its entirety.

As used herein, a "protein of interest" or "POI" is any protein, or functional fragment or derivative thereof, that one skilled in the art wishes to study, or for which one desires to conditionally destabilize and regulate the degradation of the protein, functional fragment or derivative thereof.

As used herein, a "degron" is an amino acid sequence that interacts with the cellular protein degradation machinery and specifies degradation of itself and any fusion protein of which it is a part.

As used herein, "preferentially binds" means to bind with greater efficiency to a subject molecule (such as a particular amino acid sequence) than another molecule. The difference in binding efficiency may be 5-fold, 10-fold, 50-fold, 100-fold, 500-fold, 1,000-fold, 10,000 fold, or more.

As used herein, "introduction of nucleic to cells" means transfection, transduction (infection), or transformation of nucleic acids (e.g., DNA) into cells, such that the nucleic acids may be used by the cell to express a protein of interest.

As used herein, "degradation" or "destruction" of a protein means its breakdown, such as by hydrolysis, into smaller proteins or amino acids, such as by the cellular proteosome. In some embodiments, the system and method described herein can also be used to indirectly regulate levels of target nucleic acids (DNA or RNA), by regulating the stability of a protein that acts directly on the stability of an RNA or DNA.

As used herein, a "light-regulated domain" or "light-regulated, stability-affecting polypeptide" may be a single polypeptide that functions as a light-dependent destabilization protein, as described herein. Such a destabilization protein may or may not require the interaction of another protein for destabilization. In some embodiments, the light-regulated, stability-affecting polypeptide merely requires exposure to light, and does not require formation of a ternary complex, as does the FKBP-rapamycin-FRB complex. A particular species is a "single-domain," light-dependent destabilization protein, wherein the single polypeptide comprises only a single domain (i.e., folded structure or functional unit as determined by X-ray crystallography, protease digestion, computer modeling, etc.).

As used herein, "fused" means arranged in-frame as part of the same contiguous sequence of amino acids in a polypeptide. Fusion can be direct such there are no additional amino acid residues or via a linker to improve performance or add functionality.

As used herein, "conservative amino acid substitutions" are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution since both are similarly-sized negatively-charged amino acids. Groupings of amino acids by physico-chemical properties are known to those of skill in the art.

As used herein, the terms "domain" and "region" are used interchangeably herein and refer to a contiguous sequence of amino acids within a POI or destabilizing domain, typically characterized by being either conserved or variable and having a defined function, such as being affected by non-toxic light of a particular wavelength, conferring stability or instability, enzymatic function, etc.

As used herein, the terms "protein" and "polypeptide" are used interchangeably and without distinction to refer to a compound made up of a chain of amino acid residues linked by peptide bonds. Unless otherwise indicated, the sequence for peptides is given in the order from the "N" (or amino) terminus to the "C" (or carboxyl) terminus. It is understood that polypeptides include a contiguous sequence of amino acid residues.

A peptide or peptide fragment is "derived from" a parent peptide or polypeptide if it has an amino acid sequence that is homologous to, but not identical to, the parent peptide or polypeptide, or of a conserved fragment from the parent peptide or polypeptide.

Two amino acid sequences or two nucleotide sequences are considered "homologous" if they have an alignment score of >5 (in standard deviation units) using the program ALIGN with the mutation gap matrix and a gap penalty of 6 or greater (Dayhoff, M. O., in Atlas of Protein Sequence and Structure (1972) Vol. 5, National Biomedical Research Foundation, pp. 101-110, and Supplement 2 to this volume, pp. 1-10.) The two sequences (or parts thereof) are more preferably homologous if their amino acids are greater than or equal to 50%, 70%, 80%, 90%, 95%, or even 98% identical when optimally aligned using the ALIGN program mentioned above.

"Modulate" intends a lessening, an increase, or some other measurable change, e.g., in the stability or biological function of a protein.

A "non-toxic light" to which a light-responsive, stability-affecting polypeptide domain responds is light of a discrete wavelength. In some embodiments, the non-toxic light has a wavelength of approximately 450-470 nm. In some embodiments, the light-responsive, stability-affecting polypeptide domain does not destabilize the protein of interest in the absence of non-toxic light of a particular wavelength. In some embodiments, the light-responsive, stability-affecting polypeptide domain destabilizes the protein of interest or fusion protein in the presence of non-toxic light of a particular wavelength to a greater degree or extent than it destabilizes the protein of interest or fusion protein in the absence of the non-toxic light.

As used herein, a "variant" protein is a protein having an amino acid sequence that does not occur in nature, as exemplified by sequences in GenBank.

As used herein, a mutant is a mutated protein designed or engineered to alter properties or functions relating to protein stabilization and/or the ability to act as a light-regulated, stability-affecting polypeptide.

II. EXEMPLARY SYSTEMS FOR CONDITIONALLY STABILIZING BIOLOGICAL MACROMOLECULES

A composition, method and a light-regulated conditional protein stability system is provided. The composition, method and system comprise a nucleic acid sequence encoding a fusion protein comprising a protein of interest fused in-frame to a light-regulated, stability-affecting polypeptide, and a non-toxic light source, wherein, upon introduction of the nucleic acid sequence to a cell, the fusion protein is expressed and the stability of the fusion protein can be modulated by exposure of the cell to a non-toxic light. The stability-affecting polypeptide, also referred to as a light-regulated, stability-affecting polypeptide, can be preselected to confer either stability or instability to the entire fusion protein, depending on the presence or absence of the light of a particular wavelength. The present composition, system and method relate to the conditional stabilization of a protein of interest (POI) fused to a light-regulated, stability-affecting polypeptide. The stability-affecting polypeptide, also referred to as the light-regulated domain or blue-light-inducible domain (B-LID), can be preselected to confer either stability or instability to the entire fusion protein, depending on the presence or absence of a particular wavelength of light that is not otherwise toxic to host cells or host organism.

Studies were performed in support of the invention, and are now described. Posttranslational regulation of protein abundance in cells is a powerful tool to study protein function. Described herein is a novel, single protein regulatory domain that is degraded upon exposure to non-toxic light. Genetic fusion of this domain to a protein of interest allows the rapid, light-induced depletion of the fusion protein in cells and higher organisms.

Methods to conditionally control protein levels in cells are essential for biologists to study complex biological systems. Several systems to regulate protein stability using cell-permeable small molecules have been developed. One system, termed the Ligand-Induced Degradation (LID) domain, is degraded together with an N-terminal fusion protein upon addition of the small molecule Shield-1. The LID domain consists of an FKBP12 protein with a 19-amino acid degron-containing peptide, TRGVEEVAEGVVLLRRRGN (SEQ ID NO: 1) fused to the C-terminus of the FKBP12 protein. The 19-amino acid peptide was found to contain a degron sequence which binds intramoleculary to the FKBP12 protein and causes the degron to be hidden from the cellular protein degradation machinery. Shield-1 binds to the same binding site as the 19-amino acid peptide. Addition of Shield-1 thereby replaces and exposes the degron causing degradation of the LID domain and N-terminal fusion protein.

A small four amino acid peptide degron, RRRG (SEQ ID NO: 2), was discovered and reported (Bonger, K. M. et al., *Nat. Chem. Biol.* 7, 531-537 (2011)), and it was shown that this degron could be fused to the C-terminal alpha helix of the AsLOV2 domain to engineer a conditional Blue-Light Inducible Degradation (B-LID) domain. This small four-amino acid peptide degron, RRRG (SEQ ID NO: 2), fused to the C-terminus of a protein of interest results in fast proteasome-mediated degradation in mammalian cells. The C-terminal alpha helix would interact with the LOV core domain in the dark state, thus sequestering the degron away from cellular quality control proteins and rendering the degron cryptic. Exposure to blue light cause the C-terminal helix to dissociate from the LOV core domain, thus revealing the degron and inducing degradation of the B-LID domain and its fusion protein through the processive activity of the proteasome (FIG. 1A).

Truncation and mutation studies of the 19-amino acid peptide revealed that the shortest possible degron is the tetrapeptide RRRG (SEQ ID NO: 2). C-terminal fusion of RRRG (SEQ ID NO: 2) to the otherwise stable yellow fluorescent protein cause strong degradation and no fluorescence is observed in 3T3 cells.

Thus, a light inducible degradation system was developed by fusing RRRG (SEQ ID NO: 2) to a plant photosensor protein domain called LOV2 (FIG. 1). This domain contains a C-terminal alpha helix that is bound tightly to the protein backbone in the dark. Illumination with non-toxic light (~450 nm) results in intramolecular addition of a cysteine sidechain to a flavin molecule causing a conformational change of the protein and undocking of the alpha helix. When the short degron is fused to the C-terminus of the alpha helix it was then found to give rise to a light dependent protein degradation domain.

In the dark, the C-terminal alpha helix interacts with the LOV core domain and the peptide degron is hidden from proteasomal recognition and degradation. Exposure to non-toxic light of a particular wavelength causes a change in the fusion protein structure, which reveals the degron, thereby inducing degradation of the B-LID domain and associated fusion protein. One B-LID system is illustrated in FIG. 1A, in which the B-LID domain is genetically fused to a protein of interest. Expression of the protein and exposure to non-toxic light causes exposure of a degron resulting in degradation of the B-LID domain and the fused protein-of-interest (POI). Cells (NIH3T3) expressing YEP-LOV24 were prepared (see Materials and Methods below), and were found to display a 5-10 fold decrease in fluorescence when exposed to blue light for two hours. Thus, expression of the fusion protein and exposure to blue light results in degradation of the fusion protein.

FIG. 1B illustrates flow cytometric and western blot analyses of the NIH3T3 cells stably expressing the YFP-LOV24 fusion construct. The cells were treated with either vehicle or 10 μM of the proteasome inhibitor MG132 and kept in dark or exposed to blue light for 2 hours and analyzed by flow cytometry and immunoblot using anti-YFP antibody (tubulin served as a loading control). The error bars in FIG. 1B represent the standard deviation of the mean based on at least two experiments. Addition of proteasome inhibitor MG132 prevents the light-dependent decrease in fluorescence by FACS analysis indicating the involvement of the proteasome upon degradation. FIG. 1C shows NIH3T3 cells expressing the YFP-LOV24 fusion protein, having been illuminated with blue light. Degradation of the fusion protein was monitored at various times after exposure to blue light using flow cytometry and Western blot analyses using an anti-YFP antibody (and tubulin as loading control). The maximum amount of YFP-LOV24 degradation was observed at approximately 90 minutes after starting illumination, and no further reduction in YPF fluorescence levels was observed when radiation was continued after this time (FIGS. 1C-1D).

Western blots were also performed to further assess the degradation of the YFP-LOV24 construct, as photobleaching of fluorescent proteins may be a concern upon continuous light exposure. To test the ability of the LOV24 domain to confer light-dependent stability to other proteins for general use of B-LID with all proteins, the LOV24 domain was fused to β-actin-mCherry fusion protein as well as to the mCherry fluorescent protein alone. Cells stably expressing these constructs were illuminated with blue light for two hours resulting in low fluorescence levels for both β-actin-mCherry-LOV24 and the mCherry-LOV24 fusion as evidenced by fluorescence microscopy, flow cytometry and immunoblot (FIGS. 2A-2C). FIG. 1D shows fluorescence micrographs of NIH3T3 cells stably expressing the YFP-LOV24 fusion. Cells were kept in the dark or illuminated with blue light for 2 hours. The Far-red fluorescent mutant "HcRed" chromoprotein serves as a marker for infection. (scalebars represent 100 μm).

Exemplary protein sequences that act as recombinantly engineered light-sensitive DDs are set forth herein as SEQ ID NOs: 3-8.

Because of the switching behavior (e.g., a light-induced structural change) in LOV2 upon treatment with a non-toxic blue light source, technologies to modulate cellular properties employing this system were developed. Many of these strategies rely on the translocation of a protein of interest (POI) by fusing an engineered LOV domain with a cellular targeting sequence to the C-terminus of the alpha helix. Additionally, successful transcription has been achieved by adding transcription factors to the alpha helix. However, the LOV domain (or any other photosensitive protein domain) has not been used to regulate proteins stability in cells, and the short degron discovered and described herein was used in further experiments, now to be described.

An advantage of the B-LID domain is its potential to regulate protein levels in transparent organisms, such as zebrafish embryos or worms. The regulation of proteins with ligands may be troublesome in these complex organisms as ligands may be toxic or not evenly distributed within the organism. In addition, light can be switched on and off easily which allows for rapid protein regulation. The feasibility of the B-LID domain was shown by injecting mRNA encoding mCherry-LOV24 into zebrafish embryos. Embryos were divided in two and grown in dark or in light. Initial fluorescence was observed at 6 hours of development for the embryos that are raised in dark and fluorescence was more apparent after 1 day (FIGS. 2A-2C). NIH3T3 cells were stably transduced with HA-mCherry-LOV24. Cells were illuminated with blue light for 2 hours and protein degradation was analyzed by fluorescence microscopy (FIG. 2A), flow cytometry (FIG. 2B) and confirmed by immunoblotting using an anti-HA antibody (FIG. 2C). The scalebar in panel (FIG. 2A) represents 25 μm. Zebrafish embryos were microinjected with mRNA encoding HA-mCherry-LOV24. Embryos were raised in the dark or exposed to blue light for the indicated times, and degradation was observed by fluorescence microscopy (FIG. 2D) and evidenced by immunoblotting using an anti-HA antibody (FIG. 2E). Scalebars represent 1 mm for images of multiple embryos and 250 μm for images of single embryos. This confirms the potential of the B-LID domain to reversibly regulate a protein of interest by light in transparent organisms. Embryos that are exposed to light at all times show low mCherry fluorescence. The degradation of mCherry-LOV24 by light was further confirmed by western blotting. Embryos were next raised in dark for 6 hours and then transferred to light to induce degradation of the readily expressed fluorescent protein. Here a significant decrease in fluorescence was observed compared to the embryos that are kept in dark.

The LOV2 domain from the phototropin 1 protein of *Avena sativa* (residues 404-546, called "AsLOV2") and truncated versions from the C-terminus of this domain were generated as recombinant constructs and the RRRG degron (SEQ ID NO: 2), or a less-strong degron, RRRGN (SEQ ID NO: 9), was fused in-frame to the C-terminus of the photo-responsive J-alpha helix (FIGS. 3A-3B). Various LOV2 domains possessing a C-terminal degron were evaluated for light-dependent stability, as described in Example 2. FIG. 3A shows an overview of the prepared mutant constructs. Two additional mutations were tested to assess the effects of flavin adduct stability (V416I) or helix binding strength to the core domain (I532A). Combinations of both mutations were also examined. FIG. 3B illustrates the analysis of protein stability, when NIH3T3 cells were stably transduced with the indicated LOV2 domain constructs with the appended degron and fused to the C-terminus of yellow fluorescent protein (YFP). The cells were treated either as normal cultured cells (grey bars) or illuminated with 465-nm light for 2 hours to facilitate analysis of protein stability. The median fluorescence intensity was measured by analytical flow cytometry. Retrovirus was used to stably transduce NIH3T3 cells with the constructs and fluorescence levels were analyzed by analytical flow cytometry. Low fluorescence was observed for all the constructs in both dark and lit states; thus the effect of a less-strong degron, RRRGN (SEQ ID NO: 9), was also investigated. Fluorescence was observed for cells that were kept in dark versus cells that were exposed to blue light for two hours, and a slight decrease in fluorescence was observed for the cells that were exposed to blue light.

These constructs were fused to the C-terminus of yellow fluorescent protein (YFP) to facilitate easy analysis of B-LID stability. NIH3T3 cells stably transduced with these constructs were analyzed by analytical flow cytometry. A blue LED light source was used to illuminate the cells. The four constructs tested (LOV5-8, FIG. 3B) displayed low fluorescence in both the dark and illuminated states, likely because the RRRG degron was too strong or insufficiently sequestered by the core LOV2 domain; thus a weaker RRRGN degron was investigated. Cells expressing YFP fused to LOV2 domains encoding the RRRGN degron displayed fluorescence when not illuminated, and a slight decrease in fluorescence was observed for cells that were exposed to blue light for two hours (LOV1-4, FIG. 3B).

In order to improve the dynamic range of the B-LID domain, the effects of mutations known to modulate the kinetic properties of the LOV domain were investigated, also as described in Example 2. A mutation (I532A) was first introduced into all eight constructs, which resulted in stronger helix binding to the core LOV2 domain with the goal of decreasing degradation in the unilluminated state. Additionally, another mutation (V416A) that lowers the rate of flavin deprotonation was explored to increase the time of degron exposure. These mutations were tested alone or in combination by transducing cells with each construct and exposing them to blue light (465 nm). Cells stably expressing these constructs displayed varying levels of light-regulated YFP expression (LOV9-32, FIG. 3B).

Figure 4B:
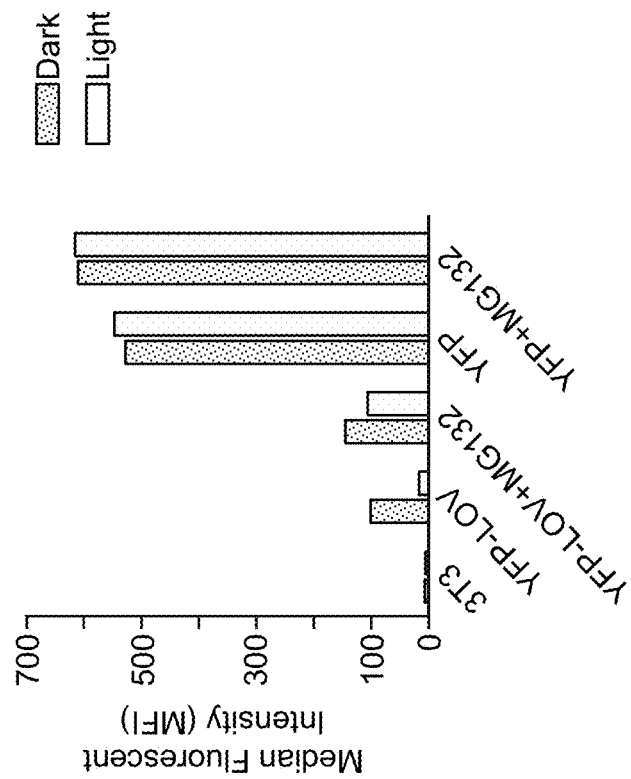
FIGS. 4A-4B show the effect of illumination with blue light for 2 hours upon protein stability.
Figure 4A:
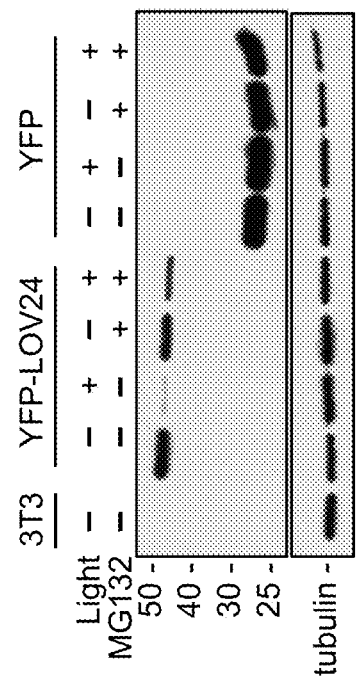

FIGS. 4A-4B show the analysis of protein stability upon illumination with blue light for 2 hours. Cells stably expressing the YFP-LOV24 fusion protein or YFP alone were treated with either vehicle or 10 µM MG132 and were kept in the dark or illuminated with blue light for 2 hours followed by analysis of YFP stability by immunoblot of cell lysates (FIG. 4A) and analytical flow cytometry of living cells (FIG. 4B). Tubulin is the loading control. Illumination with blue light exposure for 2 hours did not affect the levels of YFP as evidenced by immunoblot and flow cytometry.

FIGS. 5A-5B present the results of exposure to blue light as evidenced by microscopy and western blotting. Additional mutations to modulate the interaction between the LOV2 core domain and the degron-containing helix were tested. The nomenclature for the eight mutants tested is shown in FIG. 5A. FIG. 5B shows analytical flow cytometry of cells expressing the domains fused to the C-terminus of eYFP. The LOV24 construct displayed the best combination of stability in the dark state and instability when illuminated with blue light. The LOV24 domain lacks the last three amino acids of the original AsLOV2 domain, it contains the stronger RRRG degron, and it contains the I532A mutation which results in stronger helix binding to the AsLOV2 core domain. Additional mutations that are known to increase the helix binding affinity (e.g., the G528A/N538E tandem mutant) were also tested yet these did not improve the dynamic range of the LOV24 construct.

Figure 6:
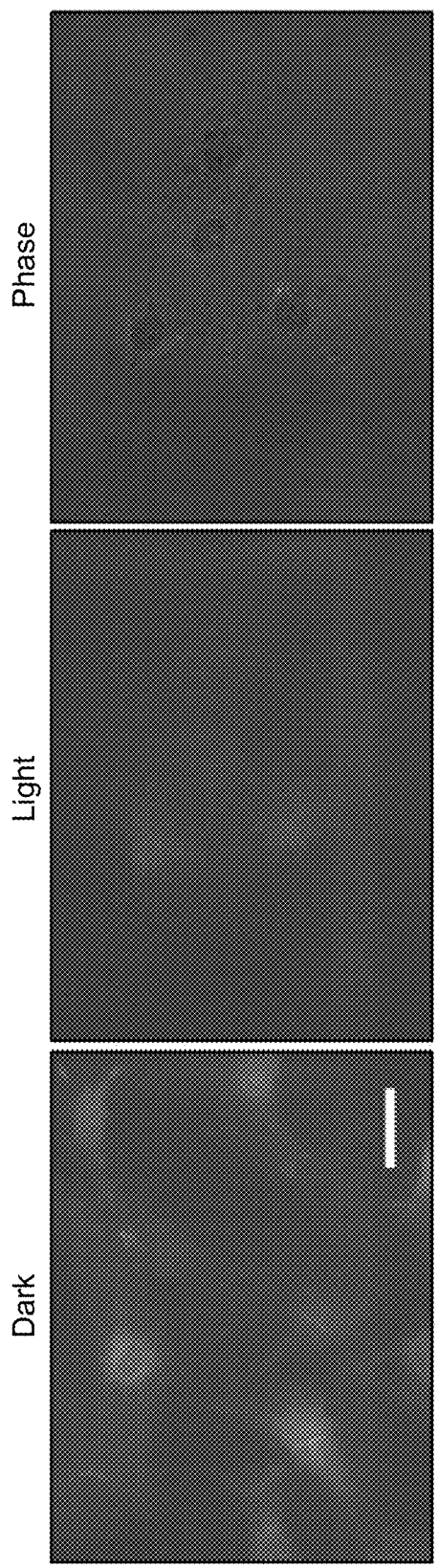
FIG. 6 is a series of three panels that show the effect of exposure to blue light on NIH3T3 cells stably transduced with β-Actin fused to mCherry-LOV24 incorporated into microfilaments.

FIG. 6 shows β-Actin fused to mCherry-LOV24, incorporated into microfilaments. NIH3T3 cells were stably transduced with β-actin-mCherry-LOV24 and kept in dark or illuminated with blue light for 2 hours. Phase contrast is shown for the cells that are exposed to light. Scalebar represents 25 µm.

Figure 7:
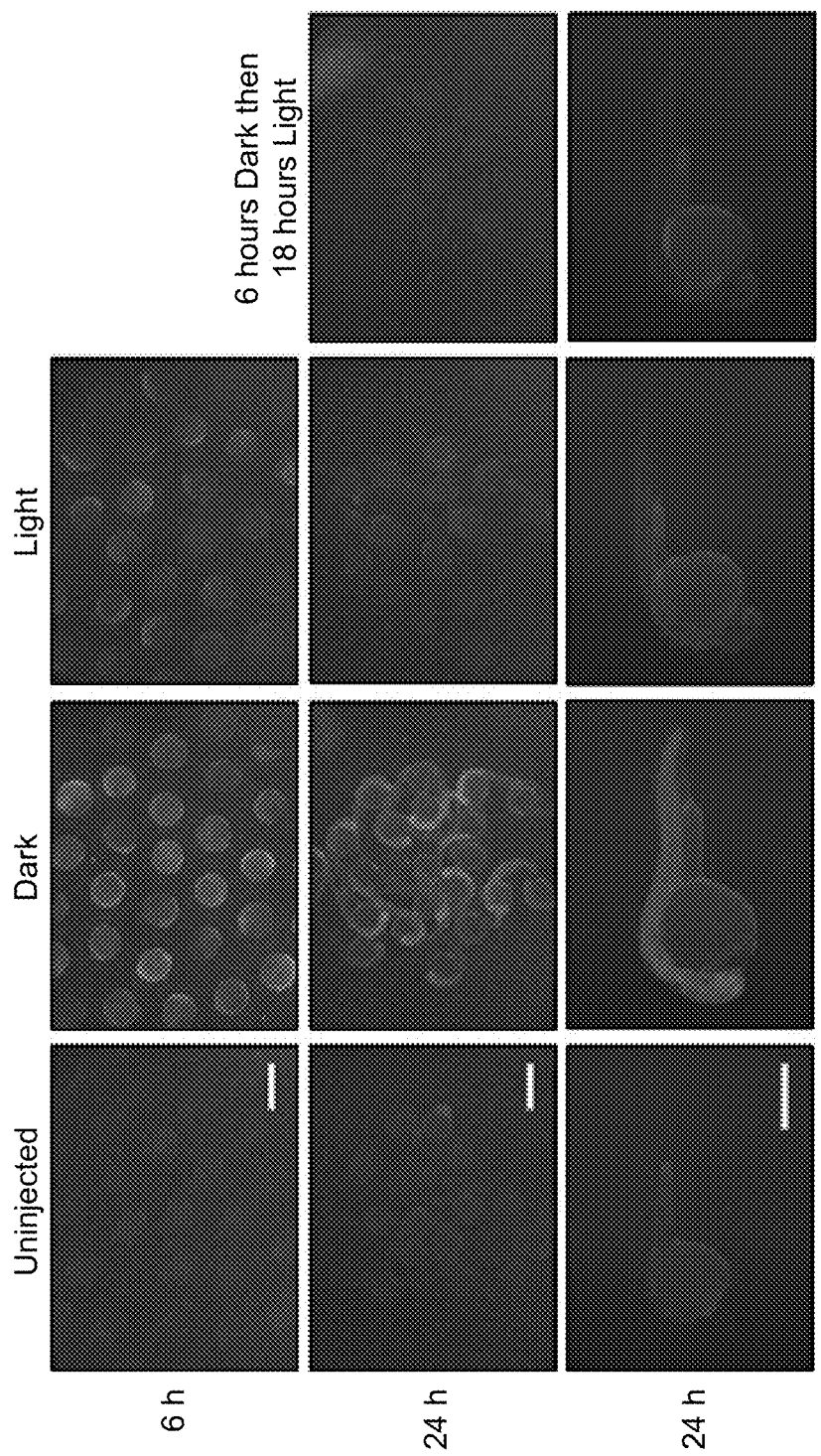
FIG. 7 illustrates the light-sensitive degradation upon illumination of Zebrafish embryos expressing of HA-mCherry-LOV24.

FIG. 7 illustrates Zebrafish embryos microinjected with mRNA encoding HA-mCherry-LOV24. Embryos were raised in the dark or exposed to blue light for the indicated times and degradation was observed by fluorescence microscopy. Zebrafish embryos that were grown in the dark for 6 hours to allow protein expression were then illuminated with the light source to evaluate the degradation of mature protein (two right-most panels). Embryos that were illuminated with blue light showed reduced fluorescence compared to embryos that were kept in the dark.

Compared to others, the B-LID technology offers several benefits. First, it is general and can be applied to any protein of interest. Second, only one genetic fusion is needed in contrast to other previously described technologies that need multiple protein domains. Lastly, the method and system described herein allow protein levels to be rapidly and reversibly controlled by light on a posttranslational level. The B-LID domain and the technology described herein are useful for studying proteins involved in neurological disorders and in neuroscience in general, where local activation of a subpopulation of cells by optogenetics has resulted in major discoveries in the field. (Fenno, L. Yizhar, O. & Deisseroth, K. *Annu Rev Neurosci.* 34, 389-412 (2011)). In addition, the fact that this technology uses only one domain to regulate protein levels may facilitate its use in transgenic animals. As described herein, the B-LID system is useful is easily adaptable for use in transparent cells and organisms. For example, this technology is useful for any eukaryotic cells in which blue light can be delivered, such as cultured cells from almost any organism, and even in large-scale industrial settings (where conditional regulation of one or more proteins in mass production are tested for integrity via their interaction with antibodies or enzymes, for example). Additionally, this technology is useful for studies of relatively optically transparent cells, organisms and animals. For example, for studies of organisms during the early stages of development, in which pigmentation is not yet a barrier to delivering light or observing the effects of the perturbation, this system and method are very attractive.

An important feature of light-regulated conditional protein alleles such as the B-LID domain is the ability to perturb these proteins in a spatially selective manner in living organisms. This can be particularly useful in transparent model organisms such as zebrafish or *C. elegans*. Illumination is instantaneous, which allows for rapid regulation of light-sensitive proteins. The use of small molecule ligands to regulate proteins may be troublesome in these organisms, as ligands may elicit unanticipated or undesired effects (e.g., toxicity) and may not be evenly distributed within the organism.

The present disclosure demonstrates the feasibility of using the B-LID domain in vivo by injecting mRNA encoding mCherry-LOV24 into zebrafish embryos. Embryos were bisected and then cultured with or without blue light illumination. Fluorescence is detectable 6 hours post-injection for embryos grown without illumination, and mCherry expression becomes more apparent after 24 hours (FIG. 2D). Embryos continually illuminated with blue light display low mCherry fluorescence at all time points, and degradation of mCherry-LOV24 by light was confirmed by immunoblotting (FIG. 2E). In another study, embryos were raised in the dark for 6 hours at which point illumination was started to light to induce degradation of the mCherry-LOV24 fusion protein (FIG. 7). A significant decrease in fluorescence was observed compared to the embryos that were not illuminated. This confirms the potential of the B-LID domain and light to reversibly regulate a protein of interest in transparent organisms.

The method presently disclosed allows protein levels to be rapidly and reversibly controlled by light on a posttranslational level. The B-LID is simple to use by fusing it to the 3'-end of any gene under study. Additionally, only one genetic manipulation is required, which makes this strategy attractive for use in organisms that are not easily amenable to high-efficiency gene targeting. Demonstrated herein is the utility of the B-LID domain in cultured cells and in zebrafish embryos, and it can be appreciated from these exemplary cells and organisms how the system can be used in other organisms. The use of a single light-sensitive domain to conditionally regulate protein stability may facilitate its use in transgenic animals.

It will be appreciated that variations of the technology disclosed herein includes replacement of the mammalian specific degron (RRRG; SEQ ID NO: 2) with degrons that can be recognized by bacteria (the YALAA peptide; SEQ ID NO: 10) or yeast (the CL1 degron).

Ideal techniques for conditionally stabilizing biological macromolecules are specific, fast, reversible, and tunable. Cell-permeable small molecules often deliver the latter three features but, apart from a few well-known exceptions, cell-permeable small molecules are typically not specific for a single biological target. The ideal conditional stabilization technology combines the specificity of reverse genetics (i.e., well-defined DNA changes in a large genomic background) with the conditionality of cell-permeable small molecules.

The present systems work in different cell types, and works in cell culture as well as in animals. The system provides heretofore unprecedented control of the levels of preselected protein in cells, with excellent dose and temporal control. While the present methods have been described with reference to the a light-regulated, stability-affecting polypeptide domain used in conjunction with non-toxic blue light with a wavelength in the range of approximately 450-470 nm, other domains and other wavelengths of light may be used. Preferred stability-affecting proteins modulate the degradation of a fusion protein, as determined, for example, using the kinetic and immunological assays described herein.

The abundance of variants obtained in the screens, as well as the ability to use different light-regulated stability affecting polypeptide domains, suggests that further refinements in screening may lead to additional stability-affecting proteins selected for various properties (e.g., rate of degradation, potency of stabilization, subcellular localization, and the like). Moreover, the stability-affecting proteins may work when fused to either the N- or the C-terminus of a POI, illustrating the modularity of the components of the system. In some embodiments, destabilizing domain described herein works when appended to the N-terminus, but not when appended to the C-terminus of a POI. In some embodiments, the destabilizing domain described herein works when appended to the C-terminus, but not when appended to the N-terminus of a POI.

Preferred stability-affecting proteins produce a 5, 10, 20, 30, 40, 50, 60, or more-fold difference in the levels of a preselected POI, which difference can be detected in cell or in an animal in the absence or presence of light of a particular wavelength. In some embodiments, the gene or allele encoding the naturally-occurring POI (i.e., the native protein, not a fusion protein) is deleted or disrupted in the genome of the cells or animal in which the conditional protein stability system is used or replaced by a DNA encoding the fusion protein. In this manner, the only source of the POI is the conditionally stabilized fusion protein, allowing its function to be studies in the absence of the interfering wild-type/naturally-occurring protein.

The stability-affecting proteins may encompass amino acid substitutions that do not substantially affect stability, including conservative and non-conservative substitutions Preferably, the amino acid sequences of the peptide inhibitors encompassed in the invention have at least about 60% identity, further at least about 70% identity, preferably at least about 75% or 80% identity, more preferably at least about 85% or 90% identity, and further preferably at least about 95% identity, to the amino acid sequences set forth herein. Percent identity may be determined, for example, by comparing sequence information using the advanced BLAST computer program, including version 2.2.9, available from the National Institutes of Health. The BLAST program is based on the alignment method of Karlin and Altschul ((1990) *Proc. Natl. Acad. Sci. U.S.A.* 87:2264-68) and as discussed in Altschul et al. ((1990) *J. Mol. Biol.* 215:403-10; Karlin and Altschul (1993) *Proc. Natl. Acad. Sci. U.S.A.* 90:5873-77; and Altschul et al. (1997) *Nucleic Acids Res.* 25:3389-3402).

Conservative amino acid substitutions may be made in the amino acid sequences described herein to obtain derivatives of the peptides that may advantageously be utilized in the present invention. Conservative amino acid substitutions, as known in the art and as referred to herein, involve substituting amino acids in a protein with amino acids having similar side chains in terms of, for example, structure, size and/or chemical properties. For example, the amino acids within each of the following groups may be interchanged with other amino acids in the same group: amino acids having aliphatic side chains, including glycine, alanine, valine, leucine and isoleucine; amino acids having non-aromatic, hydroxyl-containing side chains, such as serine and threonine; amino acids having acidic side chains, such as aspartic acid and glutamic acid; amino acids having amide side chains, including glutamine and asparagine; basic amino acids, including lysine, arginine and histidine; amino acids having aromatic ring side chains, including phenylalanine, tyrosine and tryptophan; and amino acids having sulfur-containing side chains, including cysteine and methionine. Additionally, amino acids having acidic side chains, such as aspartic acid and glutamic acid, can often be substituted with amino acids having amide side chains, such as asparagine and glutamine.

The stability-affecting proteins may be fragments of the above-described destabilizing domains, including fragments containing variant amino acid sequences. Such fragments are readily identified using the assays described herein. In some embodiments, the fragments retain the ability to undergo a structural change upon exposure to non-toxic light of a particular wavelength, with similar efficiency to the destabilizing domains described herein or with at least 90% efficiency, at least 80% efficiency, at least 70% efficiency, or even at least 50% efficiency with respect to the described stability-affecting proteins.

A related aspect of the methods and compositions are cells transfected with nucleic acids encoding a fusion protein comprising a protein of interest fused in frame to a stability-affecting protein. Expression of the fusion protein may be driven by the endogenous promoter, ideally reproducing the spatial and temporal expression patterns of the unmodified gene. The cells may be transfected, e.g., using an expression vector, or transduced (i.e., infected) using a viral vector, including but not limited to a vector derived from a retrovirus (e.g., a lentivirus), herpesvirus, pox virus, adenovirus, adenoassociated virus, or an RNA virus, such as poliovirus, flavivirus, alphavirus, or the like. The exemplary viral vector was based on a retrovirus.

The system was shown to be effective eukaryotic cells, including mammalian cells and protozoan parasites; therefore, the system can be expected to work in various eukaryotic cells, including those of humans, primates, rodents, dogs, cats, horses, cows, sheep, insects, amphibians, and apicomplexan parasites. The cells may be in culture or in a living organism. As noted above, the wild-type or naturally-occurring gene or allele encoding the POI may be deleted to facilitate study of the conditionally stabilized POI.

The present methods and compositions also allow the creation of transgenic animals harboring engineered alleles that direct the expression of a light-regulated, stability-affecting polypeptide fused to the POI. Expression of this fusion protein may be driven by the endogenous promoter, ideally reproducing the spatial and temporal expression patterns of the unmodified gene. The light may be administered regularly from an early age (including in utero) to stabilize the fusion protein until the mice achieve a specified age, at which time withdrawal of the light results in a the rapid degradation of the fusion protein. Unlike Cre-mediated gene disruption (see Background section), this method is reversible, simply by reinitiating the administration of the light, allowing the rapid, reversible, and conditional control of protein function in a complex system.

The ability to specifically and conditionally stabilize a POI in a cell enables the study of many proteins to determine their biological function and importance in a cell. The present methods and composition represent a significant improvement over current methods of conditional protein regulation.

Accordingly, based on the foregoing and on the Examples presented below, it can be seen that a method for conditionally stabilizing a protein of interest is provided. The method comprises providing a nucleic acid encoding the protein of interest in-frame to a nucleic acid encoding a light-regulated, stability-affecting polypeptide to produce a nucleic acid encoding a fusion protein; introducing the nucleic acid encoding the fusion protein into a cell; expressing the fusion protein in the cell; and exposing the cell to a non-toxic light to destabilize the fusion protein is disclosed.

The light-regulated, stability-affecting polypeptide comprises a sequence selected from the group of sequences identified by SEQ ID NOs: 3-8. The light-regulated, stability-affecting polypeptide in one embodiment is SEQ ID NO: 3.

The light sensitive degradation domain (DD) comprises a sequence selected from the group of sequences identified by SEQ ID NOs: 3-8, and a fusion protein comprising the light sensitive DD.

The cell is stably transformed with the nucleic acid, and in some embodiments, the stably transformed cell is implanted in a living animal. In some embodiments, the nucleic acid sequence is in a viral vector. In some embodiments, the viral vector is a *vaccinia* virus.

The wavelength of non-toxic light is approximately 450-470 nm, in some embodiments.

In some embodiments, introducing the nucleic acid comprises administering a viral vector comprising the nucleic acid to an animal in which the cell resides.

Also disclosed herein is a cell that comprises a nucleic acid encoding a fusion protein comprising a protein of interest fused in frame to a light-regulated, stability-affecting polypeptide.

III. KITS OF PARTS

The methods and compositions described herein may be packaged together with instructions for use, as in a kit of parts. Exemplary kits of parts include nucleic acids encoding stability-affecting proteins in-frame with a multiple cloning site and instructions for use of the kit. The instructions may contain information relating the inserting (i.e., "cloning") a POI into a plasmid, in-frame with a stability-affecting protein. The instructions may also include dosing recommendations and hardware, such as syringes, to deliver the fusion protein to an organism or to cells.

IV. EXAMPLES

The following examples, materials and methods are illustrative in nature and are not, in any way, intended to be limiting.

Materials and Methods

Reagents: Basic molecular biology reagents are used in the studies presented herein.

A. Cloning, Cell Culture, Transfections, and Transductions

All assays were performed with P20, P200, and P1000 Gilson pipetmen that were calibrated at least every 12 months. All buffers were made with deionized Milli-Q water and analytical grade reagents.

The 3'-terminus of cDNA encoding YFP (*Aequorea victoria*, GenBank DI069846) was fused to the various AsLOV2 domains, and these fusion constructs were cloned in pBMN vector with i-hcRed. Mutations were introduced with a Quikchange Site-Directed Mutagenisis Kit (Stratagene). Human β-actin fused to mCherry (Clontech) was cloned in the pBMN vector with i-Blasticidin. A 6-amino acid linker (GlyGlySerGlyGlySer, SEQ ID NO: 11) was introduced between β-actin and the fluorescent protein. The B-LID domain was fused to the C-terminus of mCherry or Actin-mCherry and an HA tag was introduced on the N-terminus of the mCherry fluorescent protein.

Genes encoding the proteins tested as fusions to the BLID domain were cloned by standard techniques in the retroviral pBMN vector encoding an iHcRed-t or iBlasticidin. The ΦNX ecotropic packaging cell line was cultured in DMEM supplemented with 10% heat-inactivated fetal bovine serum, 2 mM glutamine, 100 U/mL penicillin and 100 μg/mL streptomycin. The NIH3T3 cell line was cultured in DMEM supplemented with 10% heat-inactivated donor bovine serum, 2 mM glutamine, 100 U/mL penicillin and 100 μg/mL streptomycin. The ΦNX cells were transfected using standard Lipofectamine 2000 protocols. Viral supernatants were harvested 48 h posttransfection and filtered through a 0.45 μm nylon syringe filter. NIH3T3 cells were incubated with the retroviral supernatants supplemented with 4 μg/mL polybrene for 4-6 h at 37° C. Cells were cultured in growth media for 24 to 36 h to allow for viral integration, then assayed as described.

B. Flow Cytometry

Twenty-four hours prior to analysis, transduced NIH3T3 cells were plated at 1×10$^5$ cells per well of a 12-well plate and treated with vehicle or blue light for indicated time points prior to analysis. Cells were detached from wells of the plate using trypsin-EDTA and quenched with 1 mL of growth medium. No extra measures were taken to keep cells in dark during sample preparation. Samples were analyzed at the Stanford Shared FACS Facility with 10,000 events represented.

C. Microscopy, Immunoblotting, and Antibodies

For microscopy, NIH3T3 cells expressing fluorescent proteins were imaged with a 10×, 20× or 40× objective on a Zeiss Axioskop 2 epifluorescence microscope equipped with a QICAM FAST 1394 digital CCD camera.

For immunoblotting, NIH3T3 cells were washed in PBS and lysed on ice in MIPP buffer containing protease inhibitors. Protein concentration was measured by Bradford assay. A sample containing 5-10 μg of total protein was boiled with 5% (v/v) 2-mercaptoethanol. Samples were resolved using 9% SDS-PAGE gels and transferred to PVDF. Blots were blocked in 5% dried non-fat milk in TBS buffer containing 0.05% Tween-20, and proteins were visualized by antibodies detecting YFP, the HA epitope or β-tubulin using standard protocols.

The following antibodies were used: anti-HA (3F10, Roche Diagnostics), anti-YFP *Aequorea victoria* (JL-8, Clontech), anti-α-tubulin (Ab6046, Abeam), anti-rabbit IgG HRP (Molecular Probes), anti-mouse IgG HRP (ZYMED), anti-rat IgG HRP (Chemicon).

D. Zebrafish Microscopy and Western Blot Analysis

HA-mCherry-LOV24 mRNA was in vitro transcribed from a HA-mCherry-LOV24 PCR product with the mMessage Machine SP6 kit (Ambion) according to manufacturer's directions. For injections of mRNA, a 150-250 μM solution containing 100 mM KCl and 0.1% (w/v) phenol was prepared. One-cell stage zebrafish embryos were microinjected with this solution (1-2 nL/embryo) and embryos were divided. One dish was covered in foil (dark) and one dish was uncovered (light). Embryos from both dishes were cultured on 10 cm from the light source in E3 media to ensure a similar temperature. Embryos in which mature protein was evaluated for degradation potential were grown in dark for 6 hours and then uncovered to allow illumination.

For imaging procedures, embryos were manually dechorinated and (optionally) immobilized in E3 medium containing 0.5% (w/v) low-melt agarose and 0.05% (w/v) Tricaine mesylate. Images were acquired using a Leica M205FA fluorescence stereoscope equipped with a Leica DFC500 digital camera or a Leica DMI 6000B inverted microscope equipped with a coolsnap HQ digital camera.

For western blotting procedures, injected embryos were manually dechorionated and de-yolked in Ringers buffer containing 1 mM EDTA and 0.3 mM PMSF using a glass pipet that been drawn to have a tip diameter approximately the size of the yolk. The embryos were washed with cold Ringers containing 1 mM EDTA and 0.3 mM PMSF twice. As much liquid as possible was removed and the embryos were frozen in liquid nitrogen. The embryos were then homogenized in cold SDS-PAGE loading buffer (75 μL/50 embryos; 63 mM Tris-HCl pH 6.8, 3.5% (w/v) SDS, 10% (v/v) glycerol.) with a microfuge pestle. The sample was micofuged and the pellet was discarded. A solution of 5% (v/v) aqueous 2-mercaptoethanol was added to the supernatant and boiled for 10 minutes. Samples were resolved using 9% SDS-PAGE gels and transferred to PVDF blotting paper. Blots were blocked in 5% dried non-fat milk in TBS buffer containing 0.05% Tween-20. Proteins were visualized using antibodies to detect the HA epitopes and β-tubulin using standard protocols.

E. Blue-Light Induced Degradation

For blue-light induced degradation experiments, a commercially available blue LED light source (TaoTronics TT-AL02 Aquarium Coral Reef Tank LED Grow Light 120 W Output, Blue/White Ratio 30:25) was used. The source of non-toxic blue light had a wavelength of approximately 450-470 nm. The lamp was set so only the blue LEDs (460-470 nm, 30×3 W) were used. Cells were cultured approximately 15 cm from the light source in normal growth media. Direct illumination from the light source resulted in many dead cells, so a green filter (roscolene #781) was placed between the light source and the culture dishes. No dead cells were observed after 6 hours of illumination with such a setup. The measured power at 465 nm at a distance of 15 cm from the light source was 0.65 mW/cm$^2$ with the green filter and 8.5 mW/cm$^2$ without the green filter. To ensure similar cell growth conditions between illuminated and unilluminated cells, the cell culture dishes that were cultured without illumination were wrapped with aluminum foil and the dishes were placed in the path of the light source next to the illuminated cells.

Example 1

Using Light to Regulate Protein Stability in Cells and in Organisms

Full length (residues 404-546) as well as truncated versions of the AsLOV2 domain of phototropin 1 with the RRRG degron were fused to the C-terminus of the photo-responsive J-alpha helix. These constructs were fused to the C-terminus of yellow fluorescent protein (YFP). NIH3T3 cells were stably transduced with these constructs were analyzed by analytical flow cytometry. A blue LED light source was used to illuminate the cells. Results are shown in FIGS. 1B-1D.

The LOV24 domain was fused to a β-actin-mCherry fusion protein, as well as to the mCherry fluorescent protein alone. Cells stably expressing these constructs were illuminated with blue light for two hours resulting in low fluorescence levels for both β-actin-mCherry-LOV24 and the mCherry-LOV24 fusion as evidenced by fluorescence microscopy, flow cytometry and immunoblot, and the results are shown in FIGS. 2A-2C.

Use of the B-LID domain in vivo was studied by injecting mRNA encoding mCherry-LOV24 into zebrafish embryos. The embryos were then cultured with or without blue light illumination, and degradation was observed by fluorescence microscopy and evidenced by immunoblotting using an anti-HA antibody. Results are shown in FIGS. 2A-2E.

Example 2

Mutations

In order to improve the dynamic range of the B-LID domain, the effect of mutations known to modify the photoreceptor kinetic properties were also investigated. First, a known mutation which results in stronger helix binding to the core domain (I532A) was introduced into all constructs with the aim to decrease degradation in the dark state. (Strickland, D. et al. *Nat. Methods* 7, 623-626 (2010)). Second, a mutation known to lower the rate of flavin deprotonation was introduced (V614A) to increase the time of degron exposure. (Zoltowski, B. D., Vaccaro, B. & Crane, B. R. *Nat. Chem. Biol.* 5, 827-834 (2009)). Third, a combination of both mutations was tested. Cells were transduced with each construct and exposed to blue light for two hours. Several constructs showed fluorescence of various degrees when kept in dark and significant lower fluorescence was observed for the lit cells (FIG. 3).

YFP-LOV24 was chosen for further characterization of its kinetics and its potential applicability to other proteins of interest. This domain lacks the last three amino acids of the original AsLOV2 domain, it contains the strong RRRG degron (SEQ ID NO: 2) and a I532A mutation which results in stronger helix binding to the AsLOV2 core domain. Because of this result, other mutations known to increase the helix binding affinity (G528A,N538E tandem mutant) were also tested (Strickland, D. et al. *Nat. Methods* 7, 623-626 (2010)), but these did not result in an increased dynamic range (FIG. 4).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

---

What is claimed is:

1. A light-regulated conditional protein stability system, comprising:
a nucleic acid sequence encoding a fusion protein comprising a protein of interest fused in-frame to a light-regulated, stability-affecting polypeptide comprised of a light-sensitive degradation domain and a degron peptide selected from the group consisting of peptides identified as SEQ ID NO: 2, SEQ ID NO: 9 and SEQ ID NO: 10, wherein, upon introduction of the nucleic acid sequence to a cell, the fusion protein is expressed and stability of the fusion protein is modulated by exposure of the cell to a non-toxic light.

2. The system of claim 1, wherein the light-regulated, stability-affecting polypeptide comprises an amino acid sequence selected from the group of sequences identified by SEQ ID NOs: 3-8.

3. The system of claim 1, wherein the cell is stably transformed with the nucleic acid.

4. The system of claim 3, wherein the stably transformed cell is implanted in a living animal.

5. The system of claim 1, wherein the nucleic acid sequence is in a viral vector.

6. The system of claim 5, wherein the viral vector is a *vaccinia* virus.

7. The system of claim 1, wherein the non-toxic light has a wavelength of approximately 450-470 nm.

8. A light sensitive degradation domain (DD) comprising an amino acid sequence selected from the group of sequences identified by SEQ ID NOs: 3-8.

9. A fusion protein comprising the light sensitive DD of claim 8.

10. A cell comprising a nucleic acid encoding a fusion protein comprising a protein of interest fused in-frame to a light-regulated, stability-affecting polypeptide, wherein the light-regulated stability-affecting polypeptide is a polypeptide having 95% sequence identity to SEQ ID NO: 4, and wherein the light-regulated stability-affecting polypeptide is fused at its C-terminus to a degradation domain selected from the sequences identified as SEQ ID NO: 2 and SEQ ID NO: 9.

11. A kit of parts comprising the system of claim 1 along with instructions for use.

12. The system of claim 1, wherein the light-regulated, stability-affecting polypeptide is selected from (i) SEQ ID NO: 3 and (ii) sequences having 95% sequence identity to SEQ ID NO: 3.

13. The system of claim 1, wherein the light-regulated, stability-affecting polypeptide is selected from (i) SEQ ID NO: 4 and (ii) sequences having 95% sequence identity to SEQ ID NO: 4.

14. The light sensitive degradation domain of claim 8, wherein the light sensitive degradation domain is SEQ ID NO: 3.

15. A fusion protein comprising the light sensitive degradation domain of claim 14.

16. The system of claim 1, wherein the light-regulated stability-affecting polypeptide is a polypeptide having 95% sequence identity to SEQ ID NO: 4 fused at its C-terminus to a degradation domain selected from the sequences identified as SEQ ID NO: 2 and SEQ ID NO: 9.

17. The system of claim 1, wherein the light-regulated stability-affecting polypeptide is a sequence with 98% identity to a sequence selected from the group consisting of SEQ ID NO: 5, SEQ ID NO: 6, SEQ ID NO: 7 and SEQ ID NO: 8, the sequence fused at its C-terminus to a degradation domain selected from the sequences identified as SEQ ID NO: 2 and SEQ ID NO: 9.

* * * * *